United States Patent [19]

Schermanz et al.

[11] Patent Number: 4,812,465
[45] Date of Patent: Mar. 14, 1989

[54] TRIAZOLE DERIVATIVES FOR USE AS ANTIMYCOTIC AGENTS

[75] Inventors: Karl Schermanz, Graz; Gerald Saischek, Wels; Robert Urmann; Kurt Martetschläger, both of Linz, all of Austria

[73] Assignee: CL Pharma Aktiengesellschaft, Linz, Austria

[21] Appl. No.: 137,551

[22] Filed: Dec. 23, 1987

[30] Foreign Application Priority Data

Dec. 29, 1986 [DE] Fed. Rep. of Germany ....... 3644615

[51] Int. Cl.$^4$ ................ C07D 249/08; C07D 401/00; A61K 31/41
[52] U.S. Cl. ................................. 514/340; 548/262; 546/276; 514/383
[58] Field of Search .............. 548/262; 546/276; 514/340, 383

[56] References Cited

U.S. PATENT DOCUMENTS 4,559,077 12/1985 Regel et al. ............... 548/262

FOREIGN PATENT DOCUMENTS

| 0056860 | 8/1982 | European Pat. Off. | 548/262 |
| 0061798 | 10/1982 | European Pat. Off. | 548/262 |
| 0183147 | 6/1986 | European Pat. Off. | 548/262 |
| 3433553 | 4/1985 | Fed. Rep. of Germany | 548/262 |
| 3406908 | 9/1985 | Fed. Rep. of Germany | 548/262 |
| 2136801 | 9/1984 | United Kingdom | 548/262 |
| 2175899 | 12/1986 | United Kingdom | 548/262 |

OTHER PUBLICATIONS

H. Buchel, "The History of Azole Chemistry", 1986, pp. 11-23.

G. Jager, "The Chemistry of N–Substituted Azole Fungicides", 1983, pp. 55–65.

Godefroi et al., J. Med. Chem. 1969, pp. 784–791.

Primary Examiner—Mary C. Lee
Assistant Examiner—Robert C. Whittenbaugh
Attorney, Agent, or Firm—Mark Dryer

[57] ABSTRACT

Imidazole and triazole derivatives of the general formula

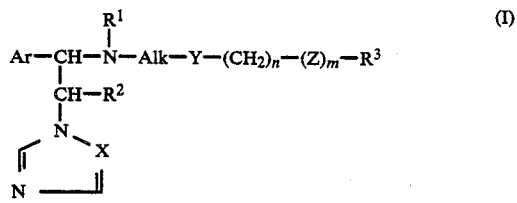

in which Ar denotes thienyl or denotes phenyl, biphenylyl or naphthyl, each of which is substituted by halogen, lower alkyl or lower alkoxy, $R_1$ denotes hydrogen or lower alkyl, Alk denotes straight-chain or branched alkyl having 1 to 10 carbon atoms, Y denotes oxygen, sulfur, sulfinyl or sulfonyl, n denotes zero, 1 or 2, Z denotes oxygen, sulfur or sulfinyl, m denotes zero or 1, $R_3$ denotes hydrogen, straight-chain or branched alkyl, cyclohexyl, or denotes phenyl which is optionally substituted by hydroxyl, halogen, trifluoromethyl, lower alkyl or lower alkoxy, or denotes biphenlyl, pyridyl or denotes naphthyl which is optionally substituted by halogen, X denotes CH or N, and $R_2$ denotes hydrogen or lower alkyl, and their pharmaceutically acceptable acid addition salts for use as antimycotic agents in human and veterinary medicine.

9 Claims, No Drawings

TRIAZOLE DERIVATIVES FOR USE AS ANTIMYCOTIC AGENTS

The invention relates to imidazole and triazole derivatives for use as antimycotic agents, and to the use of these compounds for the preparation of antimycotic agents.

EP-A-183,147 describes β-substituted aminophenethylazole derivatives which are used as fungicides for agriculture and horticulture. It is disclosed in H. Büchel: Fungicide Chemistry Advances and Practical Applications, Am. Chem. Soc. Washington 1986, pages 11–23, and G. Jäger, Pesticide Chemistry: Human Welfare and the Environment, vol. I, 55–56, Pergamon Press Oxford 1983, that despite great structrual similarity within the azole class of compounds there are often great differences in the biological properties, and compounds effective as fungicides in agriculture are not necessarily suitable for use as antimycotics in human and veterinary medicine. Imidazole and triazole derivatives, some of which are new, have now been found and have excellent antimycotic properties for use in human and veterinary medicine.

Accordingly, the invention relates to imidazole and triazole derivatives of the formula I

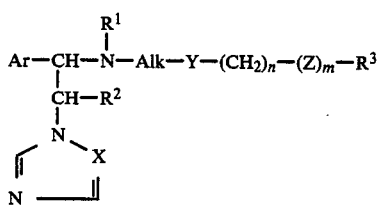

in which Ar denotes thienyl or denotes phenyl, biphenylyl or naphthyl, each of which is substituted by halogen, lower alkyl or lower alkoxy, $R_1$ denotes hydrogen or lower alkyl, Alk denotes straight-chain or branched alkylene having 1 to 10 carbon atoms, Y denotes oxygen, sulfur, sulfinyl or sulfonyl, n denotes zero, 1 or 2, Z denotes oxygen, sulfur or sulfinyl, m denotes zero or 1, $R_3$ denotes hydrogen, straight-chain or branched alkyl, cyclohexyl, or denotes phenyl which is optionally substituted by hydroxyl, halogen, trifluoromethyl, lower alkyl or lower alkoxy, or denotes biphenylyl, pyridyl or denotes naphthyl which is optionally substituted by halogen, X denotes CH or N, and $R_2$ denotes hydrogen or lower alkyl, and to their pharmaceutically acceptable acid addition salts for use as antimycotic agents.

The substances according to the invention can be prepared by reacting compounds of the formula II

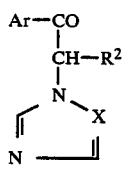

in which Ar and X have the above meaning, with compounds of the formula III

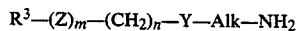

in which $R_3$, Z, m, n, Y and Alk have the above meaning, where appropriate in the presence of an inert diluent, reducing the resulting imino compounds of the formula IV

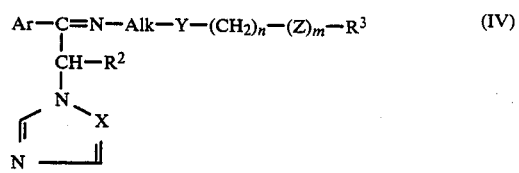

in which Ar, Alk, Y, Z, $R_2$, $R_3$, n and m have the above meaning, where appropriate in the presence of an inert diluent, and, if desired, converting the resulting compounds of the formula I in which $R_1$ denotes hydrogen, by customary alkylation methods, into compounds of the formula I in which $R_1$ denotes lower alkyl.

Compounds II and III are reacted by, for example, heating the reaction mixture in an organic diluent. If compounds III are used in the form of their salts, then addition of one equivalent of a base, such as trialkylamine, sodium alcoholate or alkali metal hydroxide, is necessary.

Diluents which are used are aliphatic or aromatic hydrocarbons, which may be chlorinated, such as petroleum fractions, perchloroethylene, benzene, toluene, chlorobenzene, xylene, ethers such as dibutyl ether or dioxane, alcohols such as butanol, pentanol or ethylene glycol, amides such as dimethylformamide, and mixtures thereof with the abovementioned diluents. The components are heated under reflux with a water trap until no more water of reaction separates out. The imino compound IV obtained after removal of the diluent is dissolved or suspended in an organic diluent, followed by cooling. Diluents which are used are, in particular, alcohols, preferably methanol, or ethers such as diethyl ether or tetrahydrofuran. The reduction is then carried out by addition of a reducing agent, in particular a complex metal hydride such as, for example, alkali metal borohydride, alkali metal cyanoborohydride, aluminum borohydride or lithium aluminum hydride, preferably sodium borohydride, at a temperature of, say, between −20° C. and the reflux temperature of the diluent used, preferably at a temperature of −5° C. to +20° C.

All conventional methods of alkylation are suitable for introducing the alkyl radical $R_1$. For example, to introduce the methyl radical it is possible to add aqueous formaldehyde solution to a compound of the formula I in which $R_1$ denotes hydrogen in an alcoholic, for example methanolic, solution, to heat the mixture to boiling, and, after the reaction solution has cooled, to allow a reducing agent, preferably sodium borohydride, to act on it.

In another process, the compounds of the general formula I are obtained by reacting a compound of the general formula II with an aminoalkanol of the formula V

reducing the imino compound which is obtained as reaction product of the formula VI

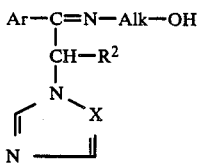

(VI)

converting the resulting hydroxyalkylamino compound of the formula VII

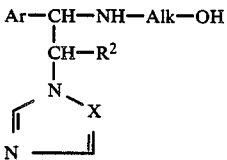

(VII)

into the corresponding halogenoalkylamino compound of the general formula VIII

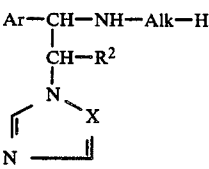

(VIII)

reacting the latter with a compound of the formula IX $$HY-(CH_2)_n-(Z)_m-R^3 \quad (IX)$$

and, if desired, converting the resulting compounds of the formula I in which $R_1$ denotes hydrogen, by customary alkylation methods, into compound of the formula I in which $R_1$ denotes lower alkyl, where Ar, Alk, Y, Z, $R_2$, $R_3$, n and m in the above formulae V to IX have the meaning indicated for formula I, and Hal represents halogen.

The reaction of a compound of the formula II with an amino alcohol of the general formula V is carried out in an organic diluent at a temperature between 0° C. and 180° C., preferably at the reflux temperature of the diluent used. The diluents which are used are aliphatic or aromatic hydrocarbons, which may be chlorinated, such as petroleum fractions, perchloroethylene, benzene, toluene, xylene, chlorobenzene, ethers such as dibutyl ether or dioxane, alcohols such as butanol, pentanol or ethylene glycol, amides such as dimethylformamide, and mixtures thereof with the abovementioned diluents. The imino compound VI obtained after removal of the diluent is dissolved or suspended in an organic diluent, and the solution or suspension is cooled. The diluents which are used are, in particular, alcohols, preferably methanol, or ethers such as diethyl ether or tetrahydrofuran. The reduction is carried out by addition of a reducing agent, preferably a complex metal hydride, in particular sodium borohydride, at a temperature from about −20° C. to the reflux temperature of the diluent used, preferably at a temperature of about −5° C. to +20° C. The hydroxyalkylamino compound VII which is obtained after the customary working up is dissolved in an organic diluent, preferably in a chlorinated aliphatic hydrocarbon, for example chloroform, and the solution is cooled. The hydroxyl compound VII is converted into the corresponding halogen compound VIII by addition of a halogenating agent, for example phosphorus tribromide, the reaction being carried out at a temperature of about −50° C. to room temperature, preferably from −20° C. to 0° C. The reaction of the compound of the general formula VIII with the compound of the general formula IX is preferably carried out in alcoholic, for example methanolic, solution in the presence of a base, for example sodium methylate or alkali metal hydroxide, at a temperature of about −20° C. to 120° C., preferably at a temperature of 20° C. to 80° C.

$R_1$ and $R_2$, independently of one another, in the formulae I to IX denote a hydrogen atom or an alkyl radical having 1 to 4 C atoms, preferably a hydrogen atom or the methyl radical. Ar denotes phenyl, biphenylyl, naphthyl or thienyl, each of which is substituted by halogen, lower alkyl or lower alkoxy, preferably 2,4-dichlorophenyl.

Alk denotes a straight-chain or branched, saturated hydrocarbon radical having 1 to 10 C atoms. Examples of such radicals are methyl, ethyl, n-propyl, i-propyl, butyl, s-butyl, t-butyl radicals, and straight-chain or branched pentyl, hexyl, heptyl and octyl radicals.

Y denotes oxygen, sulfur, sulfinyl or sulfonyl, particularly preferably sulfur. Z can denote oxygen, sulfur or sulfinyl. $R_3$ denotes a hydrogen atom, a straight-chain or branched hydrocarbon radical having 1 to 12 C atoms, a cyclohexyl radical, phenyl or naphthyl radicals which can be sub-stituted once or several times by halogen atoms, hydroxyl groups, alkyl or alkoxy radicals having 1-4 C atoms or trifluoromethyl, or denotes biphenylyl or pyridyl, prefer-ably 4-chlorophenyl, 4-bromophenyl, 4-iodophenyl, 4-methoxyphenyl, 4-methylphenyl, 2,4-, 3,4- or 2,6-di-chlorophenyl, 2-methyl-4-chlorophenyl, cyclohexyl or naphthyl.

The agents according to the invention have interesting antimycotic properties and can be used as medicaments. This action has been demonstrated by determination of the minimum inhibitory concentration (MIC) for yeasts, molds and dermatophytes.

The agents according to the invention can be used in the customary manner as solid, semisolid or liquid formulations in the form of tablets, capsules, powders, suppositories, solutions, creams, lotions, gels, ointments or the like. Pharmaceutically tolerated non-toxic vehicles or excipients which are normally used for solid formulations are tricalcium phosphate, calcium carbonate, kaolin, bentonite, talc, gelatin, lactose and starch and the like. Examples of those suitable for semisolid formulations are water, vegetable oils and low-boiling solvents such as i-propanol, hydrogenated naphthalenes and the like.

The agents according to the invention can be subjected to conventional pharmaceutical measures, such as sterilization, and can contain conventional pharmaceutical additives such as preservatives, stabilizers, emulsifiers, salts for adjusting the osmotic pressure, and buffers. The agents can also contain other therapeutically active materials besides the compounds according to the invention.

The agents according to the invention are normally composed of a pharmaceutically tolerated nontoxic vehicle in conjunction with one or more compounds according to the invention in an effective amount which results in alleviation or prevention of the specific conditions to be treated. Since the active compounds according to the invention exhibit an antimycotic action over a wide concentration range, the effective amount may vary. For example, the amount for topical formulations may be approximately 0.1 to 10% of the total pharmaceutical formulation, whereas in other formulations the amount may be approximately 5 to about 95% or more. It is preferable, to facilitate administration, to formulate the pharmaceutical agents according to the invention as dosage unit.

The agents according to the invention can be administered for pharmaceutical use in humans and animals in a conventional manner, for example: topically, orally, parenterally or in a similar manner. The exact schedule for the pharmaceutical administration of the compounds and agents according to the invention necessarily depends on the requirements of the individual case, the nature of the treatment, which, for example, may be preventive or curative, and the nature of the organisms involved.

For systemic, for example oral or parenteral, administration, it is generally appropriate to administer the active compound in amounts of about 1–120 mg/kg of body weight per day, preferably 5–100 mg/kg of body weight per day, it also being possible to distribute these amounts over several doses (for example 3 per day) in order to achieve good results. However, for localized administration correspondingly less active compound is necessary.

EXAMPLE 1

(Compound No. 1)

(a) Preparation of the intermediate 1-(2-(2,4-Dichlorophenyl)-2-(3-(4-bromophenylthio)-propylimino)ethyl)-1H-imidazole 14.8 g (0.058 mole) of 2,4-dichlorophenacylimidazole, 16.8 g (0.059 mole) of 4-bromophenylthiopropylamine hydrochloride and 6.0 g (0.059 mole) of triethylamine are suspended or dissolved in 100 ml of toluene, and the mixture is heated under reflux with a water trap until no more water of reaction separates out. The reaction solution is then washed with water, the org. phase is dried with sodium sulfate and, after the solvent has been evaporated off, 27.9 g of 1-(2-(2,4-dichlorophenyl)-2-(3-(4-bromophenylthio)propylimino)ethyl)-1H-imidazole are obtained as a viscous oil. (Yield: 98%).

(b) Preparation of the final product 1-(2-(2,4-Dichlorophenyl)-2-(3-(4-bromophenylthio)-propylamino)ethyl)-1H-imidazole 27.9 g (0.057 mole) of 1-(2-(2,4-dichlorophenyl)-2-(3-(4-bromophenylthio)propylimino)ethyl)-1H-imidazole are dissolved in 150 ml of methanol, the solution is cooled to −5° C., and 6.4 g (0.169 mole) of sodium borohydride are added in portions in such a way that the temperature does not rise above 5° C. The reaction mixture is subsequently stirred at 30° C. for a further 1 hour, then evaporated to dryness and the pH is adjusted to 1 with half-concentrated hydrochloric acid. Subsequently the reaction solution is adjusted to a pH of about 12 with 40% strength sodium hydroxide solution and is extracted several times with dichloromethane. After the combined extracts have been washed with water and dried, and the solvent has been removed in vacuo there is obtained an oil from which, by treatment with acetone and nitric acid, 10.6 g of pure dinitrate of 1-(2-(2,4-dichloro-phenyl)-2-(3-(4-bromophenylthio)-propylamino)ethyl)-1H-imidazole of melting point 162°–179° C. are obtained. (Yield: 32%).

EXAMPLE 2

(Compound No. 2)

(a) Preparation of the intermediate 1-(2-(2,4-Dichlorophenyl)-2-(3-hydroxypropylimino)ethyl)-1H-imidazole (Compound No. 50)

153.2 g (0.60 mole) of N-(2,4-dichlorophenacyl)imidazole and 53.0 g (0.705 mole) of 3-amino-1-propanol are suspended or dissolved in 400 mol of toluene, and the mixture is heated under reflux with a water trap until no more water of reaction separates out. The reaction solution is then washed 3 times with water, the organic phase is dried with sodium sulfate and, after the solvent has been evaporated off, 179 g of 1-(2-(2,4-dichlorophenyl)-2-(3-hydroxypropylimino)ethyl)-1H-imidazole are obtained as a highly viscous oil. (Yield: 95.6%).

1-(2-(2,4-Dichlorophenyl)-2-(3-hydroxypropylamino)ethyl)-1H-imidazole 179.0 g (0.5737 mole) of 1-(2-(2,4-dichlorophenyl)-2-(3-hydroxypropylimino)ethyl)-1H-imidazole are dissolved in 300 ml of methanol, the solution is cooled to 0° C., and 50.0 g (1.322 mole) of sodium borohydride are added in portions in such a way that the temperature does not rise above 5° C. After the borohydride has been added, the reaction mixture is stirred at room temperature for a further 2 hours, then evaporated to dryness, and the pH is adjusted to 1 with half-concentrated hydrochloric acid. Subsequently, the reaction solution is adjusted to a pH of about 12 with 40% strength sodium hydroxide solution, and is extracted several times with dichloromethane. After the combined organic extracts have been washed with water and dried, and the solvent has been removed in vacuo, 169 g of crude product are obtained as an oil. Recrystallization of the oil from acetone results in 107 g of pure 1-(2-(2,4-dichlorophenyl)-2-(3-hydroxypropylamino)ethyl)-1H-imidazole of melting point 77°–79° C. (Yield: 51%).

1-(2-(2,4-Dichlorophenyl)-2-(3-bromopropylamino)ethyl)-1H-imidazole 12.6 g (0.04 mole) of 1-(2-(2,4-dichlorophenyl)-2-(3-hydroxypropylamino)ethyl)-1H-imidazole are dissolved in 30 ml of chloroform, and the solution is cooled to −5° C. While stirring, 10.83 g of phosphorus tribromide, dissolved in 20 ml of CHCl$_3$, are slowly added dropwise in such a way that the temperature does not rise above 0° C. After the dropwise addition, 100 ml of petroleum ether are added to the reaction mixture, resulting in 20.5 g of crystalline 1-(2-(2,4-dichlorophenyl)-2-(3-bromopropylamino)ethyl)-1H-imidazole as the dihydrobromide of melting point 140°–150° C., and this is immediately reacted further, for reasons of stability. (Yield: 95%).

(b) Preparation of the final product 1-(2-(2,4-Dichlorophenyl)-2-(3-(4-chlorophenylthio)-propylamino)-1H-imidazole 5.4 g (0.01 mole) of freshly prepared 1-(2-(2,4-dichlorophenyl)-2-(3-bromopropylamino)ethyl)-1H-imidazole dihydrobromide and 1.45 g (0.01 mole) of 4-chlorothiophenol are dissolved in 50 ml of methanol, and 6 ml of a 30% strength solution of sodium methylate are added. The reaction mixture is heated to reflux for 2 hours and then stirred at room temperature for a further 14 hours. Subsequently the methanol is evaporated off in vacuo, the residue is taken up in dichloromethane, and the organic phase is shaken with 5% strength sodium hydroxide solution and washed with water. After drying and removal of the solvent in vacuo, the residue is dissolved in acetone, and concentrated nitric acid is added dropwise, resulting in 3.0 g of 1-(2-(2,4-dichlorophenyl)-2-(3-(4-chlorophenylthio)-propylamino)ethyl)-1H-imidazole as the dinitrate. Recrystallization from alcohol results in 2.2 g of colorless crystals of melting point 168°–177° C. (Yield: 41%).

EXAMPLE 3

(Compound No. 3):

Preparation of the N-alkyl compounds 1-(2-(2,4-Dichlorophenyl)-2-(N-methyl-3-(4-chlorobenzylthio)propylamino)ethyl)-1H-imidazole 8.18 g (0.018 mole) of 1-(2-(2,4-dichlorophenyl)-2-(3-(4-chlorobenzylthio)propylamino)ethyl)-1H-imidazole are dissolved in 100 ml of methanol, 34.3 g of 35% strength aqueous formaldehyde solution are added, and the mixture is boiled for 2 hours. The reaction solution is cooled and then 14.6 g of sodium borohydride are added, and the mixture is stirred at room temperature of 14 hours. Subsequently the methanol is evaporated off in vacuo, half-concentrated hydrochloric acid is added to the residue, and then 40% strength sodium hydroxide solution is added until the pH is 12, and the mixture is extracted 3 times with dichloromethane. The combined extracts are washed with water and then the solvent is evaporated off in vacuo, resulting in an oil. The crude product is chromatographed on silica gel (mobile phase: ethyl acetate/methanol=10:1). An oil is obtained and is treated with ethanolic hydrochloric acid to result in 2.0 g of 1-(2-(2,4-dichlorophenyl)-2-(N-methyl-3-(4-chlorobenzylthio)propylamino)ethyl)-1H-imidazole as the dihydrochloride of melting point 170°–180° C. (Yield: 21%).

The following compounds were obtained by one of the indicated processes:

TABLE I $R_2 = H$

| No. | Ar | $R_1$ | Alk | Y | n | Z | $R_3$ | X | Salt | Melting point °C. |
|---|---|---|---|---|---|---|---|---|---|---|
| 4 | 2,4-dichlorophenyl | H | —$(CH_2)_2$— | O | — | — | H | N | — | 98 |
| 5 | 2,4-dichlorophenyl | H | —$(CH_2)_2$— | O | — | — | H | CH— | | viscous oil |
| 6 | 2,4-dichlorophenyl | H | i-propylene | O | — | — | H | CH— | | viscous oil |
| 7 | 2,4-dichlorophenyl | H | i-butylene(2) | O | — | — | H | CH— | | oil |
| 8 | 2,4-dichlorophenyl | H | —$(CH_2)_2$— | O | 2 | O | H | N | — | 77–78 |
| 9 | 2,4-dichlorophenyl | H | —$(CH_2)_2$— | O | 2 | O | H | CH— | | oil |
| 10 | 2,4-dichlorophenyl | H | —$(CH_2)_2$— | O | — | — | phenyl | CH2HCl | | 140–145 |
| 11 | 2,4-dichlorophenyl | H | —$(CH_2)_2$— | O | — | — | phenyl | N | 2HNO$_3$ | 163–166 |
| 12 | 2,4-dichlorophenyl | H | —$(CH_2)_2$— | O | — | — | 4-fluorophenyl | N | 2HNO$_3$ | 163–188 |
| 13 | 2,4-dichlorophenyl | H | —$(CH_2)_2$— | O | — | — | 4-fluorophenyl | CH2HNO$_3$ | | 148–168 |
| 14 | 2,4-dichlorophenyl | H | —$(CH_2)_2$— | O | — | — | 4-chlorophenyl | N | HCl | 155–158 |
| 15 | 2,4-dichlorophenyl | H | —$(CH_2)_2$— | O | — | — | 4-chlorophenyl | CH2HCl | | 219–222 |
| 16 | 2,4-dichlorophenyl | H | —$(CH_2)_2$— | O | — | — | 4-bromophenyl | N | 2HNO$_3$ | 147–152 |
| 17 | 2,4-dichlorophenyl | H | —$(CH_2)_2$— | O | — | — | 4-bromophenyl | CH2HCl | | 200–210 |
| 18 | 2,4-dichlorophenyl | H | —$(CH_2)_2$— | O | — | — | 2,4-dichlorophenyl | CHHCl | | resin |
| 19 | 2,4-dichlorophenyl | H | —$(CH_2)_2$— | O | — | — | 2,4-dichlorophenyl | CH2HCl | | resin |
| 20 | 2,4-dichlorophenyl | H | —$(CH_2)_2$— | O | — | — | 3,4-dichlorophenyl | CHH2C$_2$O$_4$·½H$_2$O | | 185–187 |
| 21 | 2,4-dichlorophenyl | H | —$(CH_2)_2$— | O | 2 | S | 4-chlorophenyl | N | HNO$_3$.H$_2$O | 148–157 |
| 22 | 2,4-dichlorophenyl | H | —$(CH_2)_2$— | O | 2 | S | 4-chlorophenyl | CH2HNO$_3$ | | 81–85 |
| 23 | 2,4-dichlorophenyl | H | —$(CH_2)_2$— | S | — | — | 2-methylpropyl | N | 2HNO$_3$ | 146–153 |
| 24 | 2,4-dichlorophenyl | H | —$(CH_2)_2$— | S | — | — | 2-methylpropyl | CHH2C$_2$O$_4$ | | 185–195 |
| 25 | 2,4-dichlorophenyl | H | —$(CH_2)_2$— | S | — | — | dodecyl | N | 2HNO$_3$ | 111–125 |
| 26 | 2,4-dichlorophenyl | H | —$(CH_2)_2$— | S | — | — | dodecyl | CH2HNO$_3$ | | 122–124 |
| 27 | 2,4-dichlorophenyl | H | —$(CH_2)_2$— | S | — | — | cyclohexyl | N | 2HNO$_3$ | 158–171 |
| 28 | 2,4-dichlorophenyl | H | —$(CH_2)_2$— | S | — | — | cyclohexyl | CH2HNO$_3$ | | 149–160 |
| 29 | 2,4-dichlorophenyl | H | —$(CH_2)_2$— | S | — | — | p-tolyl | N | — | viscous oil |
| 30 | 2,4-dichlorophenyl | H | —$(CH_2)_2$— | S | — | — | p-tolyl | N | 2HNO$_3$ | 134–149 |
| 31 | 2,4-dichlorophenyl | H | —$(CH_2)_2$— | S | — | — | 4-chlorophenyl | N | — | 79–82 |
| 32 | 2,4-dichlorophenyl | H | —$(CH_2)_2$— | S | — | — | 4-chlorophenyl | CH2HCl.H$_2$O | | 124–127 |
| 33 | 2,4-dichlorophenyl | H | —$(CH_2)_2$— | S | — | — | 4-chlorophenyl | N | 2HCl | 145–149 |
| 34 | 2,4-dichlorophenyl | H | —$(CH_2)_2$— | S | — | — | 4-chlorophenyl | CH2HCl | | 206–212 |
| 35 | 2,4-dichlorophenyl | H | i-butylene(2) | S | — | — | 4-chlorophenyl | CH2HNO$_3$ | | 143–147 |
| 36 | 2,4-dichlorophenyl | H | —$(CH_2)_2$— | S | — | — | 4-bromophenyl | N | 2HNO$_3$ | 154–165 |
| 37 | 2,4-dichlorophenyl | H | —$(CH_2)_2$— | S | — | — | 4-bromophenyl | CH2HNO$_3$ | | 183–186 |
| 38 | 2,4-dichlorophenyl | H | —$(CH_2)_2$— | S | — | — | 4-methoxyphenyl | N | HCl | 135–145 |
| 39 | 2,4-dichlorophenyl | H | —$(CH_2)_2$— | S | — | — | 4-methoxyphenyl | CH2HNO$_3$ | | 168–174 |
| 40 | 2,4-dichlorophenyl | H | —$(CH_2)_2$— | S | — | — | 2-naphthyl | CH2HNO$_3$ | | 188–195 |
| 41 | 4-biphenylyl | H | —$(CH_2)_2$— | S | 1 | — | phenyl | N | — | viscous oil |
| 42 | 2,4-dichlorophenyl | H | —$(CH_2)_2$— | S | 1 | — | phenyl | N | 2HNO$_3$ | 120–128 |
| 43 | 2,4-dichlorophenyl | H | —$(CH_2)_2$— | S | 1 | — | phenyl | CH2H2C$_2$O$_4$.H$_2$O | | 156 |
| 44 | 2,4-dichlorophenyl | H | —$(CH_2)_2$— | S | 1 | — | phenyl | CH— | | viscous oil |
| 45 | 2,4-dichlorophenyl | H | —$(CH_2)_2$— | S | 1 | — | 4-chlorophenyl | N | 2HNO$_3$ | 152–153 |
| 46 | 2,4-dichlorophenyl | H | —$(CH_2)_2$— | S | 1 | — | 4-chlorophenyl | CH2HNO$_3$ | | 157–161 |
| 47 | 2,4-dichlorophenyl | H | —$(CH_2)_2$— | S | 1 | — | 4-trifluoromethyl-phenyl | CH— | | viscous oil |
| 48 | 2,4-dichlorophenyl | H | —$(CH_2)_2$— | O | 2 | SO | 4-chlorophenyl | CH— | | resin |
| 49 | 2,4-dichlorophenyl | H | —$(CH_2)_3$— | O | — | — | H | N— | | 81–83 |
| 50 | 2,4-dichlorophenyl | H | —$(CH_2)_3$— | O | — | — | H | CH— | | 77–79 |
| 51 | 2,4-dichlorophenyl | H | —$(CH_2)_3$— | O | — | — | phenyl | H | 2HNO$_3$ | 175–188 |
| 52 | 2,4-dichlorophenyl | H | —$(CH_2)_3$— | O | — | — | p-tolyl | N | 2HNO$_3$ | 130–140 |
| 53 | 2,4-dichlorophenyl | H | —$(CH_2)_3$— | O | — | — | p-tolyl | CH2HNO$_3$ | | 185–200 |
| 54 | 2,4-dichlorophenyl | H | —$(CH_2)_3$— | O | — | — | 4-t-butylphenyl | N | 2HCl | 133–141 |

TABLE I-continued $R_2 = H$

| No. | Ar | $R_1$ | Alk | Y | n | Z | $R_3$ | X | Salt | Melting point °C. |
|---|---|---|---|---|---|---|---|---|---|---|
| 55 | 2,4-dichlorophenyl | H | —(CH$_2$)$_3$— | O | — | — | 4-t-butylphenyl | CH | 2HCl | 193–203 |
| 56 | 2,4-dichlorophenyl | H | —(CH$_2$)$_3$— | O | — | — | 4-fluorophenyl | CH | 2HNO$_3$ | 152–160 |
| 57 | 2,4-dichlorophenyl | H | —(CH$_2$)$_3$— | O | — | — | 4-chlorophenyl | N | HCl | 185–191 |
| 58 | 2,4-dichlorophenyl | H | —(CH$_2$)$_3$— | O | — | — | 4-chlorophenyl | CH— | | oil |
| 59 | 2,4-dichlorophenyl | H | —(CH$_2$)$_3$— | O | — | — | 4-chlorophenyl | CH | 2HCl | 212–217 |
| 60 | 2,4-dichlorophenyl | CH$_3$ | —(CH$_2$)$_3$— | O | — | — | 4-chlorophenyl | CH | 2HCl | 210–215 |
| 61 | 2,4-dichlorophenyl | CH$_3$ | —(CH$_2$)$_3$— | O | — | — | 4-bromophenyl | N | HCl | 178–188 |
| 62 | 2,4-dichlorophenyl | CH$_3$ | —(CH$_2$)$_3$— | O | — | — | 4-bromophenyl | N | 2HCl | 193–200 |
| 63 | 2,4-dichlorophenyl | CH$_3$ | —(CH$_2$)$_3$— | O | — | — | 4-bromophenyl | CH | 2HCl | 215–220 |
| 64 | 2,4-dichlorophenyl | CH$_3$ | —(CH$_2$)$_3$— | O | — | — | 4-iodophenyl | N | 2HNO$_3$ | 143–159 |
| 65 | 2,4-dichlorophenyl | CH$_3$ | —(CH$_2$)$_3$— | O | — | — | 4-iodophenyl | CH | 2HNO$_3$ | 188–190 |
| 66 | 2,4-dichlorophenyl | CH$_3$ | —(CH$_2$)$_3$— | O | — | — | 4-methoxyphenyl | N | 2HNO$_3$ | 123–128 |
| 67 | 2,4-dichlorophenyl | H | —(CH$_2$)$_3$— | O | — | — | 4-methoxyphenyl | CH | 2HNO$_3$ | 168–188 |
| 68 | 2,4-dichlorophenyl | H | —(CH$_2$)$_3$— | O | — | — | 4-chloro-2-methylphenyl | N | 2HNO$_3$ | 151–157 |
| 69 | 2,4-dichlorophenyl | H | —(CH$_2$)$_3$— | O | — | — | 4-chloro-2-methylphenyl | CH | 2HNO$_3$ | 169–186 |
| 70 | 2,4-dichlorophenyl | H | —(CH$_2$)$_3$— | O | — | — | 2,4-dichlorophenyl | N | HCl | viscous oil |
| 71 | 2,4-dichlorophenyl | H | —(CH$_2$)$_3$— | O | — | — | 2,4-dichlorophenyl | CH | 2HCl | 203–207 |
| 72 | 2,4-dichlorophenyl | H | —(CH$_2$)$_3$— | O | — | — | 2,6-dichlorophenyl | N | 2HNO$_3$ | 176–188 |
| 73 | 2,4-dichlorophenyl | H | —(CH$_2$)$_3$— | O | — | — | 2,6-dichlorophenyl | CH | 2HCl | 191–193 |
| 74 | 2,4-dichlorophenyl | H | —(CH$_2$)$_3$— | O | — | — | 2,6-dichlorophenyl | CH | 2HCl | 191–127 |
| 75 | 2,4-dichlorophenyl | H | —(CH$_2$)$_3$— | O | — | — | biphenyl | N | 2HNO$_3$ | 144–155 |
| 76 | 2,4-dichlorophenyl | H | —(CH$_2$)$_3$— | O | — | — | biphenyl | CH | 2HNO$_3$ | 194 (decomposition) |
| 77 | 2,4-dichlorophenyl | H | —(CH$_2$)$_3$— | O | — | — | 6-bromo-2-naphthyl | N | 2HNO$_3$ | 197–198 |
| 78 | 2,4-dichlorophenyl | H | —(CH$_2$)$_3$— | O | — | — | 6-bromo-2-naphthyl | CH | 2HNO$_3$ | 199–203 |
| 79 | 2,4-dichlorophenyl | H | —(CH$_2$)$_3$— | O | — | — | 6-bromo-2-naphthyl | CH | 2HCl | 190–195 |
| 80 | 2,4-dichlorophenyl | H | —(CH$_2$)$_3$— | S | — | — | 2-methyl-2-butyl | N | 2HNO$_3$ | 152–158 |
| 81 | 2,4-dichlorophenyl | H | —(CH$_2$)$_3$— | S | — | — | 2-methyl-2-butyl | CH | H$_2$C$_2$O$_4$ | 178–181 |
| 82 | 2,4-dichlorophenyl | H | —(CH$_2$)$_3$— | S | — | — | octyl | N | 2HNO$_3$ | 124–125 |
| 83 | 2,4-dichlorophenyl | H | —(CH$_2$)$_3$— | S | — | — | octyl | CH | 2HNO$_3$ | 164–170 |
| 84 | 2,4-dichlorophenyl | H | —(CH$_2$)$_3$— | S | — | — | dodecyl | N | 2HNO$_3$ | 121–123 |
| 85 | 2,4-dichlorophenyl | H | —(CH$_2$)$_3$— | S | — | — | dodecyl | CH | 2HNO$_3$ | 118–143 |
| 86 | 2,4-dichlorophenyl | H | —(CH$_2$)$_3$— | S | — | — | cyclohexyl | N | 2HNO$_3$ | 158 |
| 87 | 2,4-dichlorophenyl | H | —(CH$_2$)$_3$— | S | — | — | cyclohexyl | CH | 2HNO$_3$ | 170–174 |
| 88 | 2,4-dichlorophenyl | H | —(CH$_2$)$_3$— | S | — | — | phenyl | N | HCl.HNO$_3$ H$_2$O | 116–131 |
| 89 | 2,4-dichlorophenyl | H | —(CH$_2$)$_3$— | S | — | — | phenyl | N | 2HNO$_3$ | 98–114 |
| 90 | 2,4-dichlorophenyl | H | —(CH$_2$)$_3$— | S | — | — | phenyl | CH | 2HCl.H$_2$O | resin |
| 91 | 2,4-dichlorophenyl | H | —(CH$_2$)$_3$— | S | — | — | 4-tolyl | N | 2HNO$_3$ | 148–154 |
| 92 | 2,4-dichlorophenyl | H | —(CH$_2$)$_3$— | S | — | — | 4-tolyl | CH | 2HNO$_3$ | 196–200 |
| 93 | 2,4-dichlorophenyl | H | —(CH$_2$)$_3$— | S | — | — | 4-fluoromethyl | N | 2HNO$_3$.H$_2$O | 131–139 |
| 94 | 2,4-dichlorophenyl | H | —(CH$_2$)$_3$— | S | — | — | 4-fluoromethyl | CH | 2HNO$_3$ | 160–165 |
| 95 | 2,4-dichlorophenyl | H | —(CH$_2$)$_3$— | S | — | — | 4-chlorophenyl | N | 2H$_2$SO$_4$ | 172–175 |
| 96 | 2,4-dichlorophenyl | H | —(CH$_2$)$_3$— | S | — | — | 4-chlorophenyl | CH | 2HCl | 193–200 |
| 97 | 2,4-dichlorophenyl | H | —(CH$_2$)$_3$— | SO | — | — | 4-chlorophenyl | CH— | | viscous oil |
| 98 | 2,4-dichlorophenyl | H | —(CH$_2$)$_3$— | SO$_2$ | — | — | 4-chlorophenyl | CH— | | viscous oil |
| 99 | 4-chlorophenyl | H | —(CH$_2$)$_3$— | S | — | — | 4-chlorophenyl | N— | | 82 |
| 100 | 4-bromophenyl | H | —(CH$_2$)$_3$— | S | — | — | 4-chlorophenyl | CH— | | viscous oil |
| 101 | tolyl | H | —(CH$_2$)$_3$— | S | — | — | 4-chlorophenyl | CH— | | viscous oil |
| 102 | 4-methoxyphenyl | H | —(CH$_2$)$_3$— | S | — | — | 4-chlorophenyl | N— | | viscous oil |
| 103 | thienyl | H | —(CH$_2$)$_3$— | S | — | — | 4-chlorophenyl | CH— | | viscous oil |
| 104 | 2,4-dichlorophenyl | H | —(CH$_2$)$_3$— | S | — | — | 4-bromophenyl | N | 2HNO$_3$ | 154–165 |
| 105 | 2,4-dichlorophenyl | H | —(CH$_2$)$_3$— | S | — | — | 4-bromophenyl | CH | 2HCl | 178–187 |
| 106 | 2,4-dichlorophenyl | H | —(CH$_2$)$_3$— | S | — | — | phenolyl | N | 2HCL.1.5H$_2$O | 108–112 |
| 107 | 2,4-dichlorophenyl | H | —(CH$_2$)$_3$— | S | — | — | phenolyl | CH | 2HCl | 202–216 |
| 108 | biphenylyl | H | —(CH$_2$)$_3$— | S | — | — | 4-chlorophenyl | CH | 2HCl | 190–192 |
| 109 | 1-naphthyl | H | —(CH$_2$)$_3$— | S | — | — | 4-fluorophenyl | CH | HCl | 153–156 |
| 110 | 1-naphthyl | CH$_3$ | —(CH$_2$)$_3$— | S | — | — | 4-fluorophenyl | CH | 2HCl | 175–190 |
| 111 | 2,4-dichlorophenyl | H | —(CH$_2$)$_3$— | S | — | — | 2,6-dichlorophenyl | N | 2HNO$_3$ | 142–150 |
| 112 | 2,4-dichlorophenyl | H | —(CH$_2$)$_3$— | S | — | — | 2,6-dichlorophenyl | CH | 2HNO$_3$ | 180–190 |
| 113 | 2,4-dichlorophenyl | H | —(CH$_2$)$_3$— | S | — | — | 2-naphthyl | N | 2HNO$_3$ | 160–165 |
| 114 | 2,4-dichlorophenyl | H | —(CH$_2$)$_3$— | S | — | — | 2-naphthyl | CH | 2HNO$_3$ | 196 |
| 115 | 2,4-dichlorophenyl | H | —(CH$_2$)$_3$— | S | — | — | 2-pyridyl | N— | | viscous oil |
| 116 | 2,4-dichlorophenyl | H | —(CH$_2$)$_3$— | S | — | — | 2-pyridyl | CH— | | viscous oil |
| 117 | 2,4-dichlorophenyl | H | —(CH$_2$)$_3$— | S | — | — | 2-pyridyl | CH | 2HNO$_3$ | 178–179 |
| 118 | 2,4-dichlorophenyl | H | —(CH$_2$)$_3$— | S | — | — | 4-pyridyl | N— | | viscous oil |
| 119 | 2,4-dichlorophenyl | H | —(CH$_2$)$_3$— | S | — | — | 4-pyridyl | CH | 3HCl.2.5 H$_2$O | deliquescent resin |
| 120 | 2,4-dichlorophenyl | H | —(CH$_2$)$_3$— | S | 1 | — | phenyl | N | 2HNO$_3$ | 138–147 |
| 121 | 2,4-dichlorophenyl | H | —(CH$_2$)$_3$— | S | 1 | — | phenyl | CH | 2HNO$_3$ | 128–137 |
| 122 | 2,4-dichlorophenyl | H | —(CH$_2$)$_3$— | S | 1 | — | 4-chlorophenyl | N | 2HNO$_3$ | 95–111 |
| 123 | 2,4-dichlorophenyl | H | —(CH$_2$)$_3$— | S | 1 | — | 4-chlorophenyl | CH | 2HNO$_3$ | 108–133 |
| 124 | 2,4-dichlorophenyl | H | —(CH$_2$)$_4$— | O | — | — | H | N | — | 84–85 |
| 125 | 2,4-dichlorophenyl | H | —(CH$_2$)$_4$— | O | — | — | H | CH— | | viscous oil |
| 126 | 2,4-dichlorophenyl | H | —(CH$_2$)$_4$— | O | — | — | 4-chlorophenyl | N | 2HNO$_3$ | 72–78 |
| 127 | 2,4-dichlorophenyl | H | —(CH$_2$)$_4$— | O | — | — | 4-chlorophenyl | CH | 2HNO$_3$ | 186–193 |
| 128 | 4-chlorophenyl | H | —(CH$_2$)$_5$— | O | — | — | H | N | — | 47 |

TABLE I-continued $R_2 = H$

| No. | Ar | $R_1$ | Alk | Y | n | Z | $R_3$ | X | Salt | Melting point °C. |
|---|---|---|---|---|---|---|---|---|---|---|
| 129 | 2,4-dichlorophenyl | H | —(CH$_2$)$_5$— | O | — | — | H | N | — | viscous oil |
| 130 | 2,4-dichlorophenyl | H | —(CH$_2$)$_3$— | O | — | — | H | CH— | — | viscous oil |
| 131 | 2,4-dichlorophenyl | H | —(CH$_2$)$_5$— | O | — | — | 4-chlorophenyl | N | 2HNO$_3$ | 140–140 |
| 132 | 2,4-dichlorophenyl | H | —(CH$_2$)$_5$— | S | — | — | 4-chlorophenyl | CH2HNO$_3$ | | 156–161 |
| 133 | 2,4-dichlorophenyl | H | —(CH$_2$)$_6$— | O | — | — | H | N | — | viscous oil |
| 134 | 2,4-dichlorophenyl | H | —(CH$_2$)$_6$— | O | — | — | H | CH— | — | viscous oil |
| 135 | 2,4-dichlorophenyl | H | —(CH$_2$)$_6$— | O | — | — | 4-chlorophenyl | N | 2NHO$_3$ | 140–160 |
| 136 | 2,4-dichlorophenyl | H | —(CH$_2$)$_6$— | S | — | — | 4-chlorophenyl | N | 2HCl | waxy |
| 137 | 2,4-dichlorophenyl | H | decylene | O | — | — | 4-chlorophenyl | N | 2HNO$_3$ | 131–144 |
| 138 | 2,4-dichlorophenyl | H | decylene | O | — | — | 4-chlorophenyl | CH2HNO$_3$ | | 114–124 |
| 139 | 1-naphthyl | H | —(CH$_2$)$_3$— | S | — | — | 4-chlorophenyl | CHHCl | | 172–176 |

EXAMPLE A

Tablet containing 200 mg of active compound for oral administration 2 g of compound No. 96 and 1 g of lactose were granulated with 1 ml of 10% strength aqueous polyvinylpyrrolidone K25 solution. The mixture was forced through a screen of mesh size 3–5 mm and was dried. This dried mixture was homogenized through a screen of mesh size 0.8–1.25 mm and then mixed with 0.58 g of microcrystalline cellulose (Avicel PH102), 30 mg of Na carboxymethyl starch and 2 mg of magnesium stearate. The resulting mixture was compressed to 10 tablets.

EXAMPLE B

1% strength solution for topical treatment

Sufficient polyethylene glycol 400 was added to a solution of 1 g of compound No. 96 in 50 ml of purified water to produce a total of 100 ml of solution.

EXAMPLE C

1% ointment for topical treatment 66 g of liquid petrolatum were melted on a waterbath with 3.5 g of Alfol 16 (cetyl alcohol) and 0.1 g of cholesterol, and a solution of 1 g of compound No. 96 in 29.4 g of purified water was added. While cooling slowly, this mixture was homogenized to produce 100 g of ointment.

EXAMPLE D

1% injection solution (ampoules containing 100 mg of active compound)

3 g of compound No. 96 and 0.3 g of a mixture of 2 parts of methyl p-hydroxybenzoate and one part of propyl p-hydroxybenzoate were dissolved and made up to 300 ml with water for injection, and the solution was filtered through a membrane filter of pore size 0.2 μm to sterilize and remove particles and then dispensed into 10 ml ampoules under aseptic conditions.

EXAMPLE E

The antimycotic activities of the compounds were measured by in vitro determination of the minimum inhibitory concentration (MIC) for yeasts, molds and dermatophytes.

6 dermatophytes, 2 yeasts and 4 molds were used for testing with fungi, as follows:

| | |
|---|---|
| Trichophyton mentagrophytes | (Tri.me.) |
| Trichophyton rubrum | (Tri.ru.) |
| Trichophyton verrucosum | (Tri.ve.) |
| Microsporum canis | (Mi.can.) |
| Epidermophyton floccosum | (Ep.flo.) |
| Microsporum gypseum | (Mi.gyp.) |
| Candida albicans | (C.alb.) |
| Candida tropicalis | (C.trop.) |
| Aspergillus fumigatus | (Asp.fu.) |
| Mucor mucedo plus | (Mu.mu$^+$) |
| Mucor mucedo minus | (Mu.mu$^-$) |
| Absidia ramosa | (Abs.ra.) |

The minimum inhibitory concentration (MIC) was determined in serial dilution tests in test tubes. The volume of the liquid nutrient medium in each test tube was 4.5 ml.

The substances were dissolved in DMSO and diluted with sterile distilled water to 10 concentrations (100, 50, 25, 12.5, 6.25, 3.12, 1.56, 0.78, 0.39 and 0.19 μg/ml). 0.5 ml of each of these dilution steps was added to liquid nutrient medium. Thus, a constant concentration of solvent in all the nutrient media was ensured, irrespective of the active compound concentration.

A comparison solution which contained only the solvent in appropriate concentration was included when carrying out each of the tests.

The individual strains were maintained on Sabouraud/beerwort agar slants and, before they were used in a test, they underwent a passage on a modified Sabouraud liquid nutrient medium. The strains were then harvested, washed and converted into a suspension of McFaerland 3 in the case of yeasts and molds and of McFaerland 4–5 in the case of dermatophytes.

The amount of material inoculated (inoculum) was 100 μl/test tube (inoculated densities: yeasts about 10$^3$/ml, molds about 10$^4$/ml, dermatophytes about 10$^4$/ml). The pH of the liquid nutrient medium was 6.0. After inoculation had taken place the fungi were incubated at 22° C. for 14 days.

The MIC was then determined. The concentration step at which growth was no longer visible on macroscopic inspection was used for the determination of the MIC. The comparison substance used was 1-(2-(2,4-dichlorophenyl)-2-(2,4-dichlorophenylmethoxy)ethyl)-1H-imidazole (compound A).

TABLE II

| Compound No. | Tri. me. | Tri. ru. | Tri. ve. | Mi. can | Ep. flo | Mi. gyp | C. alb | C. trop | Asp. fu. | Mu. mu+ | Mu. mu- | Abs. ra. |
|---|---|---|---|---|---|---|---|---|---|---|---|---|
| 34 | 0,78 | 0,78 | 0,78 | 0,78 | 0,78 | 0,78 | 3,12 | 3,12 | 6,25 | 3,12 | 3,12 | 6,25 |
| 37 | 1,56 | 1,56 | 1,56 | 6,25 | 1,56 | 0,78 | 6,25 | 6,25 | 6,25 | 6,25 | 6,25 | 12,5 |
| 39 | 6,25 | 6,25 | 6,25 | 12,5 | 12,5 | 6,25 | 25,0 | 12,5 | 12,5 | 12,5 | 12,5 | 25,0 |
| 40 | 6,25 | 3,12 | 3,12 | 3,12 | 6,25 | 3,12 | 6,25 | 6,25 | 12,5 | 12,5 | 12,5 | 12,5 |
| 90 | 25,0 | 1,56 | 1,56 | 3,12 | 3,12 | 3,12 | 6,25 | 3,12 | 3,12 | 6,25 | 3,12 | 12,5 |
| 92 | 0,78 | 0,78 | 0,78 | 3,12 | 0,78 | 0,78 | 12,5 | 12,5 | 0,78 | 0,78 | 3,12 | 6,25 |
| 94 | 6,25 | 0,78 | 0,39 | 6,25 | 3,12 | 3,12 | 12,5 | 6,25 | 12,5 | 12,5 | 12,5 | 6,25 |
| 96 | 0,39 | 0,19 | 0,39 | 0,39 | 0,19 | 0,39 | 0,39 | 0,78 | 0,78 | 1,56 | 1,56 | 1,56 |
| 2 | 12,5 | 0,19 | 0,39 | 1,56 | 6,25 | 3,12 | 3,12 | 1,56 | 3,12 | 12,5 | 25,0 | 3,12 |
| 1 | 0,39 | 0,39 | 0,30 | 1,56 | 0,78 | 0,39 | 3,12 | 1,56 | 1,56 | 6,25 | 6,25 | 3,12 |
| 112 | 3,12 | 3,12 | 3,12 | 12,5 | 3,12 | 3,12 | 6,25 | 6,25 | 12,5 | 6,25 | 12,5 | 12,5 |
| 114 | 3,12 | 1,56 | 1,56 | 0,78 | 3,12 | 3,12 | 6,25 | 6,25 | 0,78 | 6,25 | 3,12 | 6,25 |
| 3 | 6,25 | 6,25 | 6,25 | 1,56 | 1,56 | 6,25 | 3,12 | 0,78 | 25,0 | 6,25 | 6,25 | 50,0 |
| 132 | 0,78 | 3,12 | 6,25 | 12,5 | 0,78 | 3,12 | 6,25 | 3,12 | 6,25 | 0,78 | 3,12 | 6,25 |
| 14 | 12,5 | 6,25 | 12,5 | 12,5 | 3,12 | 6,25 | 12,5 | 12,5 | 100 | 12,5 | 6,25 | 100 |
| 33 | 25,0 | 3,12 | 3,12 | 6,25 | 3,12 | 6,25 | 12,5 | 6,25 | 25,0 | 6,25 | 3,12 | 25,0 |
| 36 | 25,0 | 6,25 | 12,5 | 100 | 12,5 | 6,25 | 25,0 | 12,5 | 100 | 12,5 | 50,0 | 100 |
| 52 | 6,25 | 3,12 | 3,12 | 3,12 | 3,12 | 3,12 | 12,5 | 6,25 | 6,25 | 3,12 | 12,5 | 100 |
| 62 | 1,56 | 3,12 | 1,56 | 3,12 | 0,78 | 3,12 | 6,25 | 3,12 | 1,56 | 3,12 | 3,12 | 50 |
| 67 | 100 | 25,0 | 6,25 | 50,0 | 100 | 25,0 | 100 | 50,0 | 100 | 50,0 | 50,0 | 100 |
| 68 | 25,0 | 50,0 | 6,25 | 12,5 | 25,0 | 25,0 | 50,0 | 25,0 | 100 | 6,25 | 12,5 | 100 |
| 72 | 25,0 | 3,12 | 1,56 | 25,0 | 6,25 | 6,25 | 3,12 | 3,12 | 3,12 | 6,25 | 6,25 | 100 |
| 93 | 12,5 | 6,25 | 6,25 | 25,0 | 25,0 | 25,0 | 100 | 25,0 | 100 | 25,0 | 25,0 | 100 |
| 95 | 3,12 | 1,56 | 3,12 | 6,25 | 0,78 | 3,12 | 12,5 | 12,5 | 12,5 | 3,12 | 3,12 | 100 |
| 99 | 6,25 | 3,12 | 3,12 | 12,5 | 6,25 | 3,12 | 6,25 | 12,5 | 100 | 12,5 | 6,25 | 100 |
| 104 | 25,0 | 6,25 | 12,5 | 100 | 12,5 | 6,25 | 25,0 | 12,5 | 100 | 12,5 | 50,0 | 100 |
| 126 | 50,0 | 6,25 | 3,12 | 25,0 | 12,5 | 3,12 | 25,0 | 12,5 | 25,0 | 12,5 | 25,0 | 100 |
| 67 | 50,0 | 6,25 | 6,25 | 25,0 | 50,0 | 12,5 | 25,0 | 50,0 | 25,0 | 12,5 | 12,5 | 50,0 |
| 40 | 6,25 | 3,12 | 3,12 | 12,5 | 3,12 | 3,12 | 6,25 | 25 | 6,25 | 12,5 | 25 | 12,5 |
| 100 | 6,25 | 3,12 | 6,25 | 6,25 | 6,25 | 6,25 | 3,12 | 12,5 | 6,25 | 12,5 | 25 | 6,25 |
| 105 | 0,10 | 0,10 | 0,10 | 0,78 | 0,10 | 0,39 | 3,12 | 3,12 | 0,39 | 3,12 | 3,12 | 12,5 |
| 108 | 0,78 | 1,56 | 0,78 | 6,25 | 0,78 | 3,12 | 12,5 | 3,12 | 3,12 | 6,25 | 6,25 | 50 |
| 139 | 3,12 | 1,56 | 1,56 | 1,56 | 3,12 | 1,56 | 3,12 | 12,5 | 3,12 | 3,12 | 3,12 | 3,12 |
| 103 | 12,5 | 3,12 | 3,12 | 25 | 3,12 | 6,25 | 12,5 | 25 | 12,5 | 12,5 | 12,5 | 25 |
| 56 | 3,12 | 1,56 | 1,56 | 12,5 | 6,25 | 3,12 | 12,5 | 3,12 | 0,78 | 1,56 | 0,78 | 6,25 |
| 65 | 6,25 | 0,78 | 1,56 | 1,56 | 3,12 | 3,12 | 3,12 | 1,56 | 3,12 | 6,25 | 6,25 | 3,12 |
| 60 | 6,25 | 0,78 | 1,56 | 1,56 | 3,12 | 3,12 | 3,12 | 1,56 | 6,25 | 3,12 | 1,56 | 6,25 |
| A | 1,56 | 6,25 | 6,25 | 6,25 | 1,56 | 3,12 | 12,5 | 12,5 | 3,12 | 12,5 | 12,5 | 12,5 |

EXAMPLE F

Determination of the lethal dose of 1-(2-(2,4-dichlorophenyl)-2-(3-(4-chlorophenylthio)-propylamino)ethyl)-1H-imidazole dihydrochloride (compound No. 96) in mice and rats on administration once.

In each case, oral doses of 0, 500, 1,000 and 3,000 mg/kg of body weight were administered to four groups of female and male animals.

(Control: double-distilled water)

The following clinical signs were observed.

| | | |
|---|---|---|
| Mice: | Inactivity, convulsions | |
| Rats: | Inactivity, ruffled fur, convulsions | |
| | $LD_{100}$ | |
| Mice | | |
| female | >1,000 mg/kg | <3,000 mg/kg |
| male | >500 mg/kg | <1,000 mg/kg |
| Rats | | |
| female | >500 mg/kg | <1,000 mg/kg |
| male | >1,000 mg/kg | <3,000 mg/kg |

EXAMPLE G

Determination of the $LD_{50}$ of 1-(2-(2,4-dichlorophenyl)-2-(3-(4-chlorophenylthio)propylamino)ethyl)-1H-imidazole dihydrochloride (compound No. 96) in mice and rats by i.v. administration. In each case, 0 (0.9% NaCl solution), 12.5, 25.0, 50.0 and 100 mg/kg of body weight were injected i.v. into 5 groups of female and male animals.

The following clinical signs were observed.

| | |
|---|---|
| Mice: | Inactivity, necrotic tail |
| Rats: | Inactivity, necrotic tail, convulsions |
| | $LD_{50}$ |
| Mice | |
| female | 84.1 (20.8–340.0) mg/kg |
| male | 42.0 (13.9–127.5) mg/kg |
| Rats | |
| female | 56.1 (35.4–89.1) mg/kg |
| male | 70.7 mg/kg |

EXAMPLE H

Compound No. 96 was investigated for its potential to cause gene mutations in five Salmonella typhimurium strains TA 1535, TA 1537, TA 1538, TA 98 and TA 100.

The following concentrations were tested, both with metabolic activator (S 9 mix) and without metabolic activator.

I: 10, 33.3, 100.0, 333.3, 1,000 µg/plate
II: 3.3, 10, 33.3, 100, 333.3 µg/plate No mutagenic activity whatever was observed, either with or without metabolic activator.

What we claim is:

1. A triazole derivative of the formula:

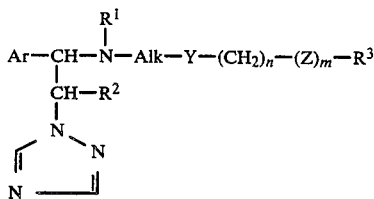

in which Ar is thienyl or is phenyl, biphenylyl or naphthyl, each of which is substituted by halogen, lower alkyl or lower alkoxy, $R^1$ is hydrogen or lower alkyl, Alk is straight-chain or branched alkylene having 1 to 10 carbon atoms, Y is oxygen, sulfur, sulfinyl or sulfonyl, n is zero 1 or 2, Z is oxygen sulfur or sulfinyl, m is zero or 1, $R^3$ is hydrogen, straight-chain or branched alkyl having 1 to 12 carbon atoms, cyclohexyl, or is phenyl which is optionally substituted by hydroxyl, halogen, trifluoromethyl, lower alkyl or lower alkoxy, or is biphenylyl, pyridyl or is naphthyl which is optionally substituted by halogen, and $R^2$ is hydrogen or lower alkyl, or a pharmaceutically acceptable acid addition salt.

2. A triazole derivative as claimed in claim 1, of the formula I in which each of $R^1$ and $R^2$ independently of one another is hydrogen or methyl.

3. A triazole derivative as claimed in claim 1, of the formula I in which Ar is 2,4-dichlorophenyl or 4-chlorophenyl.

4. A triazole derivative as claimed in claim 1, of the formula I in which Alk is —(CH$_2$)$_2$— or —(CH$_2$)$_3$—.

5. A triazole derivative as claimed in claim 1, of the formula I in which Y is oxygen or sulfur.

6. A triazole derivative as claimed in claim 1, of the formula I in which $R^3$ is phenyl, 4—Cl—, 4—Br, 4—I, 4-methoxy or 4-methylphenyl, 2,4-,3,4- or 2,6-dichlorophenyl, 2-methyl-4-chlorophenyl, cyclohexyl or naphthyl.

7. A triazole derivative as claimed in claim 1, of the formula I in which each of m and n is zero.

8. A method for the treatment or prevention of a mycotic infection in a patient which comprises administering to the patient an antimycotic-effective amount of a triazole derivative of the formula:

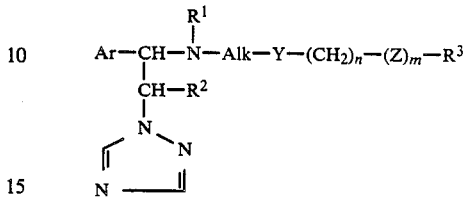

in which Ar is thienyl or is phenyl, biphenylyl or naphthyl each of which is substituted by halogen, lower alkyl or lower alkoxy, $R^1$ is hydrogen or lower alkyl, Alk is straight-chain or branched alkylene having 1 to 10 carbon atoms, Y is oxygen, sulfur, sulfinyl or sulfonyl, n is zero, 1 or 2, Z is oxygen, sulfur or sulfinyl, m is zero or 1, $R^3$ is hydrogen, straight-chain or branched alkyl having 1 to 12 carbon atoms, cyclohexyl, or is phenyl which is optionally substituted by hydroxyl, halogen, trifluoromethyl, lower alkyl or lower alkoxy, or is biphenylyl, pyridyl or is naphthyl which is optionally substituted by halogen, and $R^2$ is hydrogen or lower alkyl, or a pharmaceutically acceptable acid addition salt.

9. A method as claimed in claim 8, in which, in the compound of formula I, each of $R^1$ and $R^2$, independently of one another, is hydrogen or methyl, Ar is 2,4-dishlorophenyl or 4—chlorophenyl, Alk is (CH$_2$)$_2$— or —(CH$_2$)$_3$—, Y is oxygen or sulfur, $R^3$ is phenyl, 4—Cl—, 4—Br—, 4—I—, 4—methoxy- or 4-methylphenyl, 2,4-, 3,4-, or 2,6-dichlorophenyl, 2-methyl-4-chlorophenyl, cyclohexyl or naphthyl, and each of m and n is zero.

* * * * *